(12) United States Patent
Ko et al.

(10) Patent No.: US 10,171,072 B2
(45) Date of Patent: Jan. 1, 2019

(54) OPTIMIZED CMOS ANALOG SWITCH

(71) Applicant: Microchip Technology Inc., Chandler, AZ (US)

(72) Inventors: Isaac Ko, Kowloon (HK); Ka Wai Ho, Kowloon (HK); Wan Tim Chan, Yuen Long (HK)

(73) Assignee: MICROCHIP TECHNOLOGY INC., Chandler, AZ (US)

( * ) Notice: Subject to any disclaimer, the term of this patent is extended or adjusted under 35 U.S.C. 154(b) by 0 days.

(21) Appl. No.: 15/265,341

(22) Filed: Sep. 14, 2016

(65) Prior Publication Data

US 2017/0104481 A1 Apr. 13, 2017

(30) Foreign Application Priority Data

Oct. 8, 2015 (CN) .......................... 2015 1 0644537

(51) Int. Cl.
*H03K 17/687* (2006.01)
*A61B 8/08* (2006.01)
*H03K 17/16* (2006.01)
*A61B 8/00* (2006.01)
*H03K 17/693* (2006.01)
*H04B 1/48* (2006.01)

(52) U.S. Cl.
CPC ......... *H03K 17/161* (2013.01); *A61B 8/4483* (2013.01); *A61B 8/469* (2013.01); *A61B 8/485* (2013.01); *A61B 8/546* (2013.01); *H03K 17/6874* (2013.01); *H03K 17/693* (2013.01); *H04B 1/48* (2013.01); *H03K 2217/0054* (2013.01)

(58) Field of Classification Search
CPC ......... H03K 17/161; H03K 2217/0054; H03K 17/6871; H03K 17/6874; H03K 17/693; H04B 1/48; A61B 8/4483; A61B 8/469; A61B 8/485; A61B 8/546
See application file for complete search history.

(56) References Cited

U.S. PATENT DOCUMENTS

| | | |
|---|---|---|
| 4,595,847 A | 6/1986 | Weir |
| 5,012,123 A | 4/1991 | Ayasli et al. |
| 7,756,486 B1 | 7/2010 | Tan et al. |
| 8,368,451 B2 | 2/2013 | Mulawski et al. |
| 8,547,159 B2 | 10/2013 | Morra |
| 8,583,111 B2 | 11/2013 | Burgener |
| 9,401,659 B2 * | 7/2016 | Lei ........................ H02M 7/217 |
| 9,455,711 B2 * | 9/2016 | Kubota ............. H03K 19/0016 |
| 2015/0171898 A1 | 6/2015 | Blin et al. |
| 2016/0191036 A1* | 6/2016 | Ko ........................ H03K 17/063 600/459 |

* cited by examiner

*Primary Examiner* — Patrick O Neill
(74) *Attorney, Agent, or Firm* — DLA Piper LLP US

(57) ABSTRACT

An improved analog switch for use in an ultrasound elastography probe is disclosed. The improved analog switch results in less heat dissipation compared to prior art analog switches.

8 Claims, 7 Drawing Sheets

OPTIMIZED CMOS ANALOG SWITCH

PRIORITY CLAIM

This application claims priority to Chinese Patent Application No. 201510644537.6, filed on Oct. 8, 2015, and titled "An Optimized CMOS Analog Switch" (in Mandarin), which is incorporated herein by reference.

FIELD OF THE INVENTION

An improved analog switch for use in an ultrasound elastography device is disclosed. The improved analog switch results in less heat dissipation compared to prior art analog switches.

BACKGROUND OF THE INVENTION

Recent developments in ultrasound imaging systems include the use of shear wave elastography. FIG. 1 depicts prior art ultrasound elastography device 100, which comprises transducer 105. Transducer 105 uses acoustic radiation force to induce a "push" pulse 150 into soft tissue 110 that results in shear waves 140. Soft tissue 110 comprises stiff lesion 120 (which could be a tumor or other medical abnormality), which includes or is near region of interest 130. The tissue's stiffness is computed based upon how fast the resulting shear wave travels through the tissue. When detection pulses 160 interact with a passing shear wave 140, the passing shear wave 140 reveals the wave's location at a specific time, allowing calculation of the speed of the shear wave 140. This numerical value is related to the stiffness of the tissue within the region of interest. By using many near-simultaneous push pulses 150, and by using an advanced ultrafast imaging technique to track shear waves 140, the system can generate a two-dimensional quantitative map of the tissue's stiffness (the Young's modulus) every second.

FIG. 2 depicts certain electrical aspects of prior art ultrasound elastography device 100. Ultrasound elastography device 100 comprises an exemplary high voltage transmit path comprising amplifier 210 and diode pair 211 and an exemplary low voltage receive path comprising amplifier 250 coupled to high voltage isolation circuit 254 comprising resistors 252 and 253 and diode bridge 251. Ultrasound elastography device 100 further comprises probe selection relays 221, 222, 223, and 224, and probes 231, 232, 233, and 234. Probe 231 is shown connected to multiplexor 270, which comprises analog switches 241, 243, 245, and 247, which connect to transducers 242, 244, 246, and 248, respectively. It is to be understood that the same configuration of structures (multiplexor 270 and transducers 242, 244, 246, and 248) are used for probes 232, 233, and 234 as well. Transducer 105 in FIG. 1 is representative of transducers 242, 244, 246, and 248.

With reference to FIGS. 1 and 2, the vibration frequency of the acoustic push pulse 150 is in the 50-500 Hz range. To measure the speed of shear wave 140, each detection pulse 170 could last for 300 ms. To detect a shear wave 140, the analog switches 241, 243, 245, and 247 in the device 100 need to drive the high-voltage transducers 242, 244, 246, and 248 (represented by transducer 105) for about 300 ms.

Prior art analog switches 241, 243, 245, and 247 each requires two high-voltage switches working in parallel to avoid the excessive heat dissipation that could damage the circuits. However, two switches connected in parallel also double the parasitic capacitance and affect the image quality.

Virtually all prior art analog switches 241, 243, 245, and 247 in multiplexor 270 utilize a T-switch 300, shown in FIG. 3. In ultrasound imaging applications, the use of T-switch 300 limits the on-resistance to approximately 16 Ohms for less than 15 pF parasitic capacitance and higher than 60 dB off-isolation.

FIG. 3 shows the schematic of the conventional T-switch 300 structure used for analog switches 241, 243, 245, and 247 in high-voltage multiplexer 270. The T-switch 300 comprises NMOS transistor 310 in series with NMOS transistor 320, with shunting NMOS transistor 330 to achieve an off-isolation of 60 dB. NMOS transistors 310, 320, and 330 each comprise a thick gate oxide layer that allows for both positive and negative high gate voltage swings at the expense of on-resistance that generates excessive heat. A thick gate oxide layer typically ranges between 5000-10000 angstrom.

The high-voltage capability of the devices further worsens the on-resistance/parasitic capacitance trade-off. Fixed gate bias over the varying source voltage makes the on-resistance for positive signal much larger than that for negative signal and introduces second harmonic distortion.

FIG. 4 shows exemplary NMOS transistor 400, which is representative of NMOS transistors 310, 320, and 330. NMOS transistor 400 actually comprises NMOS transistor 410 and diode 420, which is due to the junction between the drain and the body of NMOS transistor 410. Both drain and gate are capable of operating up to 200V.

The drain/body diode structure of NMOS transistor 400 makes the high-voltage device essentially a rectifier even though it is turned off. As a result, the body of NMOS transistor 410 needs to be pulled down to the most negative voltage, e.g., −100V ($V_{NN}$) at off state just as shown in FIG. 4. Shunting NMOS transistor 330 terminates to −100V. The second series device, such as NMOS transistor 320, isolates the transducer from the −100V termination. This device is not necessary if the transducer can be terminated to −100V but that is usually not the case for the piezoelectric transducers.

Piezoelectric devices exhibit nonlinear behavior when subjected to high electric field. This strong nonlinear material behavior is induced by localized polarization switching (i.e. change of the polarization direction) at the subgrain level. Once the piezoelectric material is operating in nonlinear mode, the material likely is already damaged. Thus, terminating a piezoelectric transducer with a high voltage is destructive to the piezoelectric material. This behavior is shown in graphs 500 and 510 in FIG. 5. Graphs 500 and 510 show the change in polarization of piezoelectric material in response to a change in electric field.

An improved T-switch previously invented by the Applicant is shown in FIG. 6. T-switch 600 comprises butterfly transistor pair 615 (comprising NMOS transistors 610 and 620) in series with butterfly transistor pair 635 (comprising NMOS transistors 630 and 640) and shunt butterfly transistor pair 655 (comprising NMOS transistors 650 and 660) as shown. NMOS transistors 610, 620, 630, 640, 650, and 660 each comprise a thin gate oxide layer. A thin gate oxide layer typically ranges between 100-200 angstrom. T-switch 600 uses a lower gate voltage and has a higher transconductance than T-switch 300. Butterfly transistor pairs 615 and 635 together are comparable to a single 200V drain, 200V gate transistor in on-resistance/capacitance ratio. However, T-switch 600 experiences substantial heat dissipation.

What is needed is an improved analog switch that results in less heat dissipation than prior art T-switches 300 and 600.

SUMMARY OF THE INVENTION

The preferred embodiment is a high-voltage CMOS switch circuit topology that reduces the on-resistance to 4-8 Ohms, which is an improvement by a factor of 2 to 4 without increasing the parasitic capacitance compared to the prior art. The circuit topology is straightforward to implement and is suitable for constructing, for example, a 4:1 ultrasound multiplexer (such as multiplexor 270) that can handle analog signals of ±100 V. The power supplies to this circuit are ±6 V and the control inputs are voltage levels of 0 and +5 V, compatible with standard CMOS circuits. The circuit is particularly useful in driving high-voltage transducers for ultrasound elastography probes.

DETAILED DESCRIPTION OF THE PREFERRED EMBODIMENT

Figure 1:
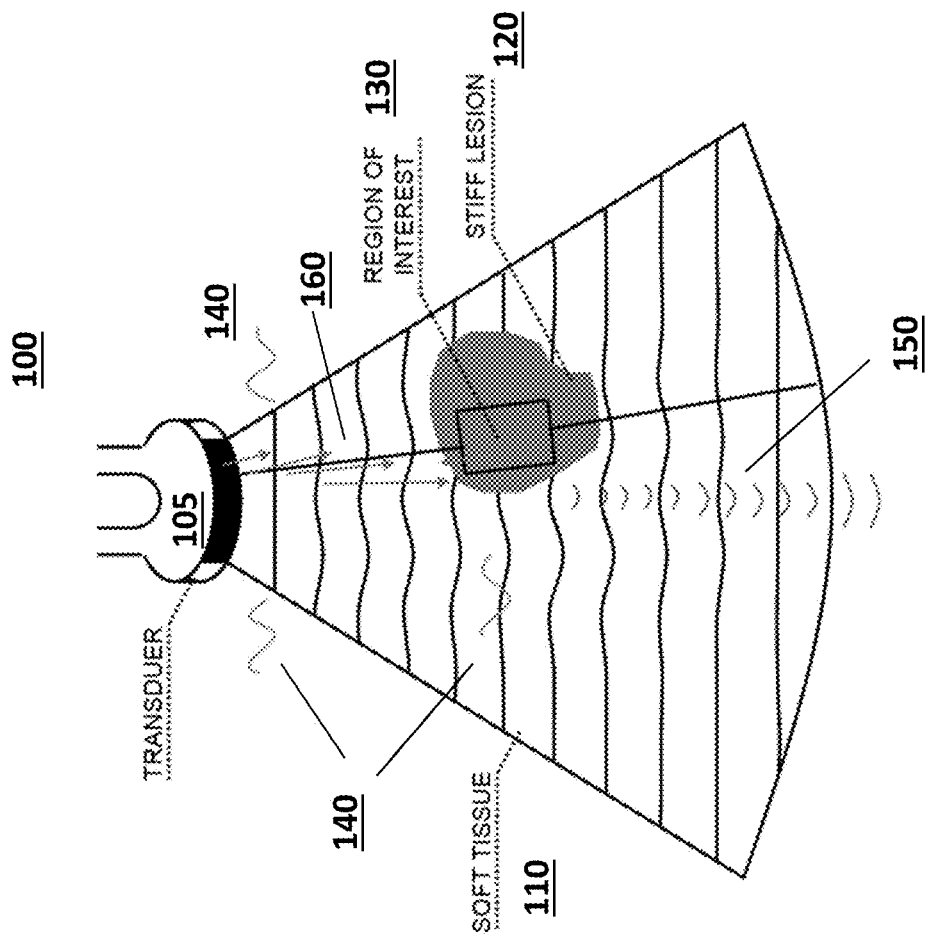
FIG. 1 depicts a prior art ultrasound elastography probe.
Figure 2:
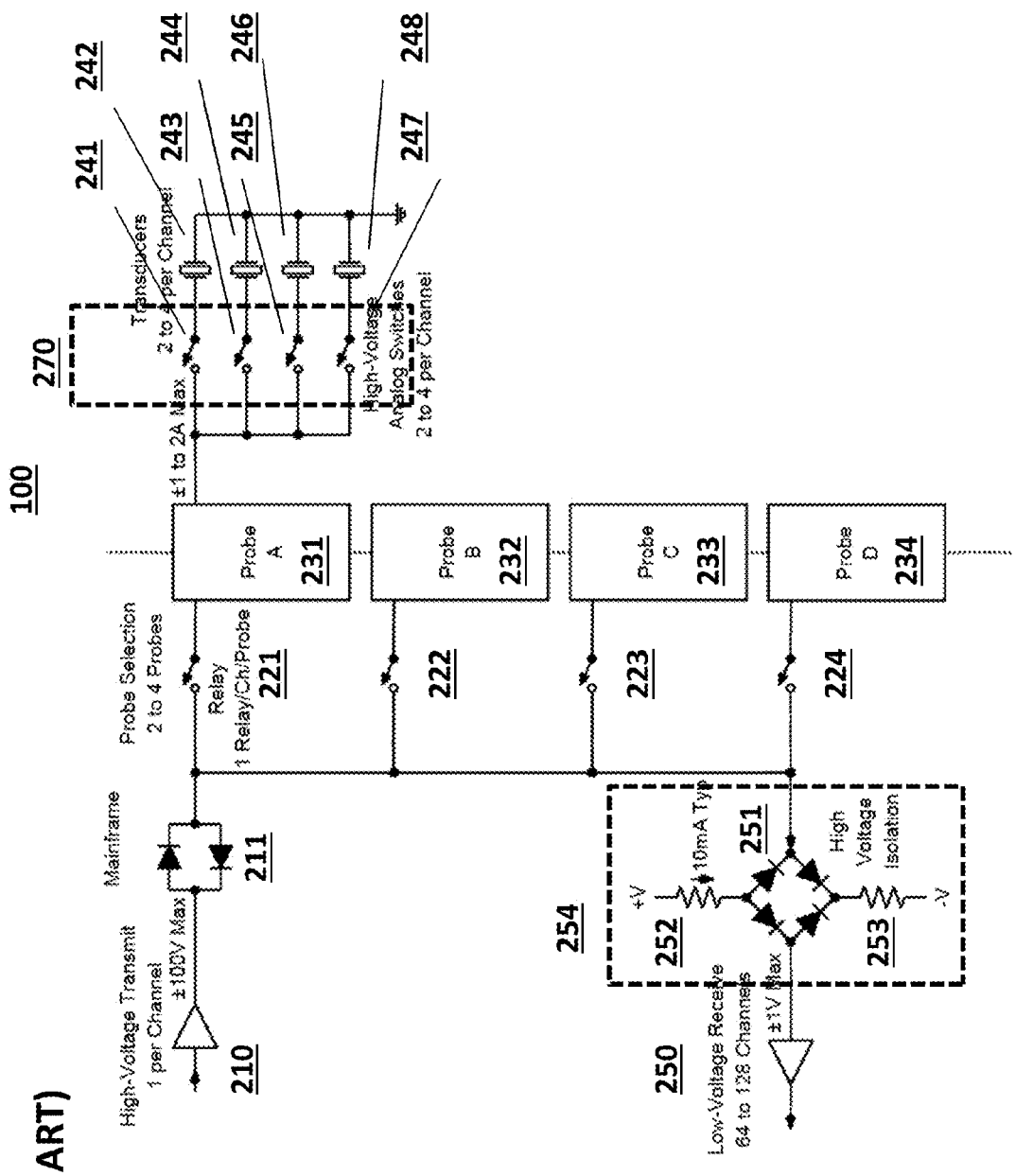
FIG. 2 depicts electrical aspects of the prior art ultrasound elastography probe.
Figure 3:
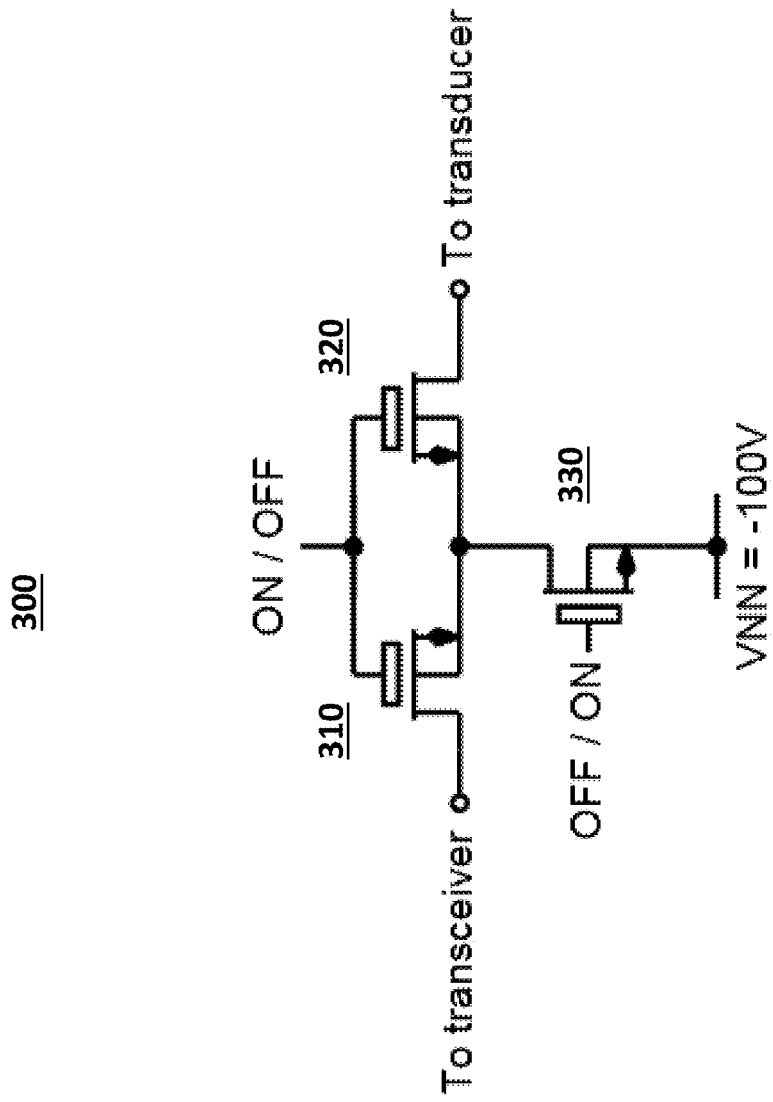
FIG. 3 depicts a prior art analog T-switch.
Figure 4:
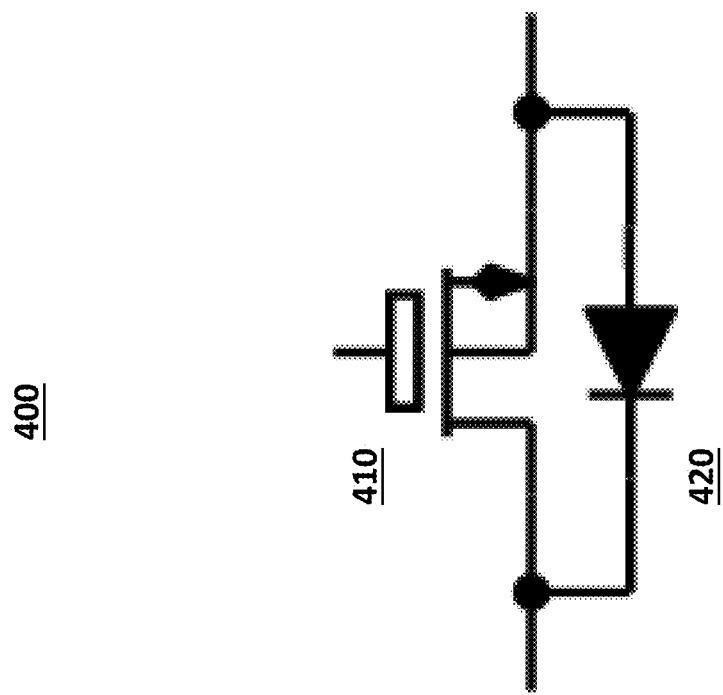
FIG. 4 depicts the structure of transistors used in the prior art analog T-switch of FIG. 3.
Figure 5:
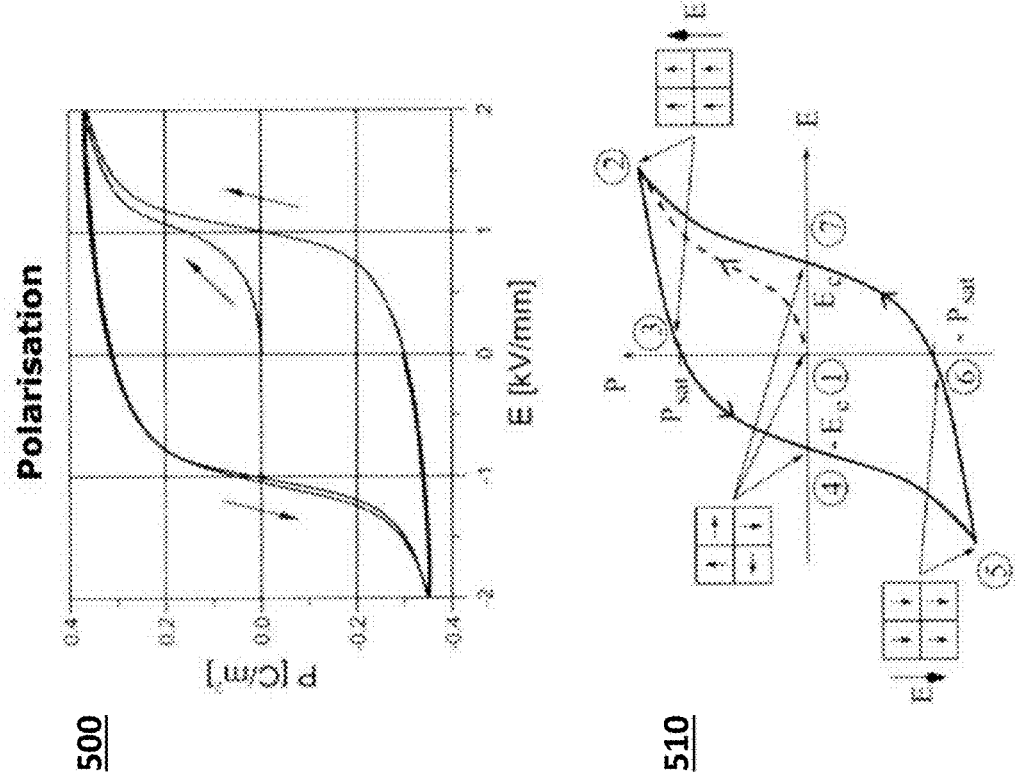
FIG. 5 depicts certain physical characteristics of prior art piezoelectric transducers.
Figure 6:
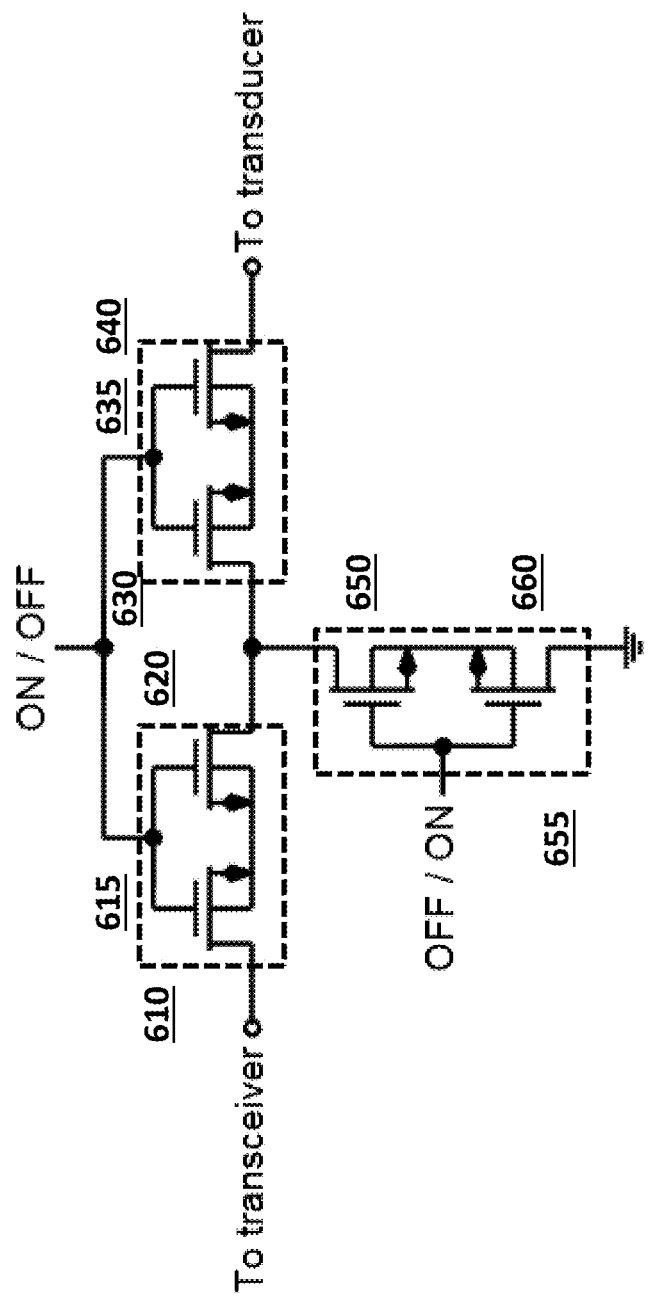
FIG. 6 depicts another prior art analog T-switch.
Figure 7:
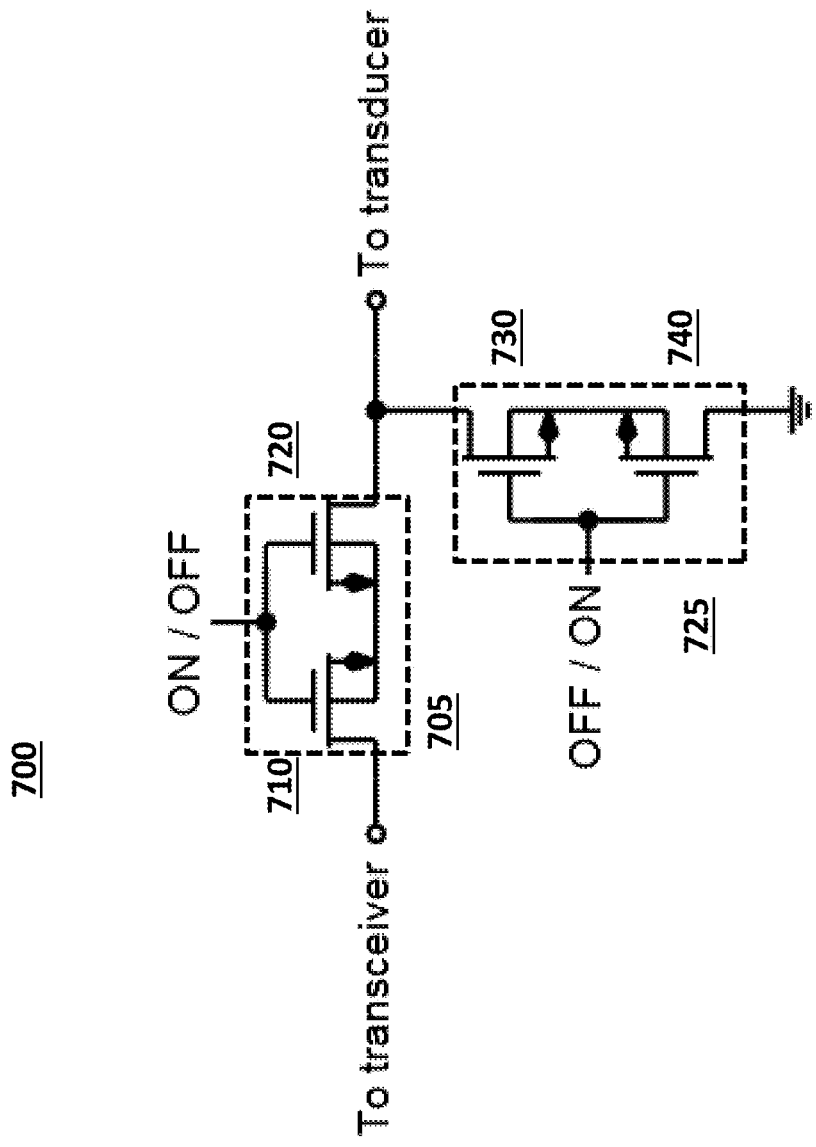
FIG. 7 depicts an embodiment of an improved analog switch.

FIG. 7 depicts an embodiment of the invention. Analog switch 700 is a modified version of T-switch 600 where one of the series butterfly transistor pairs has been removed. Analog switch 700 comprises butterfly transistor pair 705 (comprising NMOS transistors 710 and 720) and shunt butterfly transistor pair 725 (comprising NMOS transistors 730 and 740), which performs a shunting function. NMOS transistors 710, 720, 730, and 740 each comprise a thin gate oxide layer. A thin gate oxide layer typically ranges between 100-200 angstrom. In this configuration, butterfly transistor pair 705 can be considered to be a conducting means for connecting a high voltage source to a transceiver, and shunt butterfly transistor pair 725 can be considered to be a shunting means for shunting current from a terminal of the conducting means to ground.

The on-resistance of analog switch 700 is approximately half of the on-resistance of prior art T-switch 600, and the parasitic capacitance of analog switch 700 is also largely reduced compared to the parasitic capacitance of prior art T-switch 600.

The topology of analog switch 700 is immune to piezoelectric material nonlinearity issues of prior art T-switch 300, as the butterfly transistor pair 725 allows termination to ground, not to −100V as in prior art T-switch 300.

The following improvements compared to prior art T-switches 300 and 600 are achieved with analog switch 700:

(1) Can transfer voltages greater than ±100V while using only a power supply of approximately ±6V.

(2) Inputs compatible with standard 5V CMOS circuits.

(3) Analog signal capability up to 200V peak-to-peak, with peak analog signal currents of >3 A.

(4) Signal independent on-resistance lower than 8 Ohms.

(5) Parasitic capacitance reduced to 10 pF.

(6) No off-isolation concern as the non-selected transducer is terminated.

In conclusion, a high-voltage analog switch 700 using 100V thin gate oxide NMOS transistors is proposed. It is modified from a prior art T-switch 600 by removing one series device and shunting the non-selected transducer directly to ground. Circuits using this topology have wide potential application in ultrasound imaging, shear wave elastography, and even high-intensity focused ultrasound where high power ultrasound transmission is needed. For example, analog switch 700 is suitable for use in a 4:1 ultrasound multiplexer, such as multiplexor 270 in ultrasound elastography device 100.

Although the present invention has been fully described in connection with embodiments thereof with reference to the accompanying drawings, it is to be noted that various changes and modifications will become apparent to those skilled in the art. Such changes and modifications are to be understood as being included within the scope of the present invention as defined by the appended claims.

What is claimed is:

1. An analog switch, comprising:
a first butterfly circuit comprising a first thin gate oxide NMOS transistor in series with a second thin gate oxide NMOS transistor, the first butterfly circuit comprising a first terminal and a second terminal, the second terminal directly coupled to a high voltage source;
a second butterfly circuit comprising a third thin gate oxide NMOS transistor in series with a fourth thin gate oxide NMOS transistor, the second butterfly circuit comprising a third terminal directly coupled to the second terminal and a fourth terminal directly coupled to ground.

2. The switch of claim 1, wherein the on-resistance of the switch is less than 8 Ohms.

3. The switch of claim 1, wherein the parasitic capacitance of the switch is less than 10 picoFarads.

4. The switch of claim 1, wherein the high voltage source comprises a peak-to-peak amplitude greater than 200 volts.

5. The switch of claim 1, wherein the first butterfly circuit requires power supply voltages in a range between −6 volts and +6 volts.

6. The switch of claim 5, wherein the second butterfly circuit requires power supply voltages in a range between −6 volts and +6 volts.

7. An analog switch, comprising:
a conducting means for connecting a high voltage source to a transceiver; and
a shunting means for shunting current from a terminal of the conducting means to ground;
wherein the on-resistance of the switch is less than 8 Ohms.

8. An analog switch, comprising:
a conducting means for connecting a high voltage source to a transceiver; and
a shunting means for shunting current from a terminal of the conducting means to ground;
wherein the parasitic capacitance of the switch is less than 10 picoFarads.

\* \* \* \* \*